(12) United States Patent
Barrett et al.

(10) Patent No.: US 6,587,719 B1
(45) Date of Patent: Jul. 1, 2003

(54) TREATMENT OF OBESITY BY BILATERAL VAGUS NERVE STIMULATION

(75) Inventors: Burke Barrett, Houston, TX (US); Ramish K. Reddy, Brooklyn, NY (US); Mitchell S. Roslin, Neoponsit, NY (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 09/346,396

(22) Filed: Jul. 1, 1999

(51) Int. Cl.$^7$ .................................................. A61N 1/32
(52) U.S. Cl. ............................................. 607/2; 607/45
(58) Field of Search .............................. 607/2, 45, 58, 607/70, 72, 74

(56) References Cited

U.S. PATENT DOCUMENTS

| | | | |
|---|---|---|---|
| 5,188,104 A | * 2/1993 | Wernicke et al. ............ 128/419 |
| 5,330,507 A | * 7/1994 | Schwartz ...................... 607/14 |
| 5,423,872 A | * 6/1995 | Cigaina ........................ 607/40 |
| 5,514,175 A | * 5/1996 | Kim et al. .................... 607/136 |
| 5,540,730 A | * 7/1996 | Terry, Jr. et al. .............. 607/40 |
| 5,540,734 A | * 7/1996 | Zabara .......................... 607/46 |
| 5,690,691 A | * 11/1997 | Chen et al. .................... 607/40 |
| 5,792,210 A | * 8/1998 | Wamubu et al. .............. 607/58 |
| 5,913,876 A | * 6/1999 | Taylor et al. .................. 607/2 |

OTHER PUBLICATIONS

Iggo, A., Gastric Mucosal Chemoreceptors with Vagal Afferent Fibres etc., Univ. of Edinburgh (1957), 398–409.
Stacher, G. et al., Cholecystokinin Decreases Appetite and Activation etc., Brain Research Pub. (1979), 325–331.
Rohner–Jeanrenaud, F. et al., A Role for the Vagus Nerve in the Etiology etc., Int'l. J. Obesity (1985), 71–75.
Hoebel, B., Brain neurotransmitters in food and drug reward, Am. J. Clin. Nutr 42 (1985), 1133–1150.
Foltin, R. et al., Food Intake in Baboons: Effects of Long–acting Cholecystokinin Analog, Appetite (1989), 145–152.
Moran, T. et al., Potent and sustained satiety actions of cholecystokinin etc., Am. J. Clin. Nutr 55 (1992), 286S–90S.
Moran, T. et al., Blockade of type A, but not type B, CCK receptors etc., Am. Physiol. Soc. (1993), R620–R624.
Esfahani, N. et al., Inhibition of Serotonin Synthesis Attenuates etc., Pharmac Biochem Behavior 51 (1995), 9–12.
Levin, B. et al., Role of the brain in energy balance and obesity, Am. J. Physiol. 271 (1996), R491–R500.
Pierson, M., Synthesis and Biological Evaluation of Potent etc., J. Med. Chem. 40 (1997), 4302–4307.
Brownell, K. et al., ed., Eating Disorders and Obesity, Guilford Press ( ), 3–7.
Ritter S. et al., ed., Neuroanatomy and Physiology of Abdominal Vagal Afferents, CRC Press ( ), 221–248.
Matson, C., et al., Long–term CCK–leptin synergy suggets role for CCK etc., Am. J. Physiol. 276 (1999), R1038–45.
Emond, M., et al., Central leptin modulates behavioral/neural responsivity etc., Am. J. Physiol. 276 (1999), R1545–49.

* cited by examiner

Primary Examiner—Kennedy Schaetzle
(74) Attorney, Agent, or Firm—Blank Rome LLP

(57) ABSTRACT

A method of treating patients for compulsive overeating includes stimulating left and right branches of the patient's vagus nerve simultaneously with electrical pulses in a predetermined sequence of a first period in which pulses are applied continuously, alternating with a second period in which no pulses are applied. The electrical pulses are preferably applied to the vagus nerve at a supradiaphragmatic location.

28 Claims, 1 Drawing Sheet

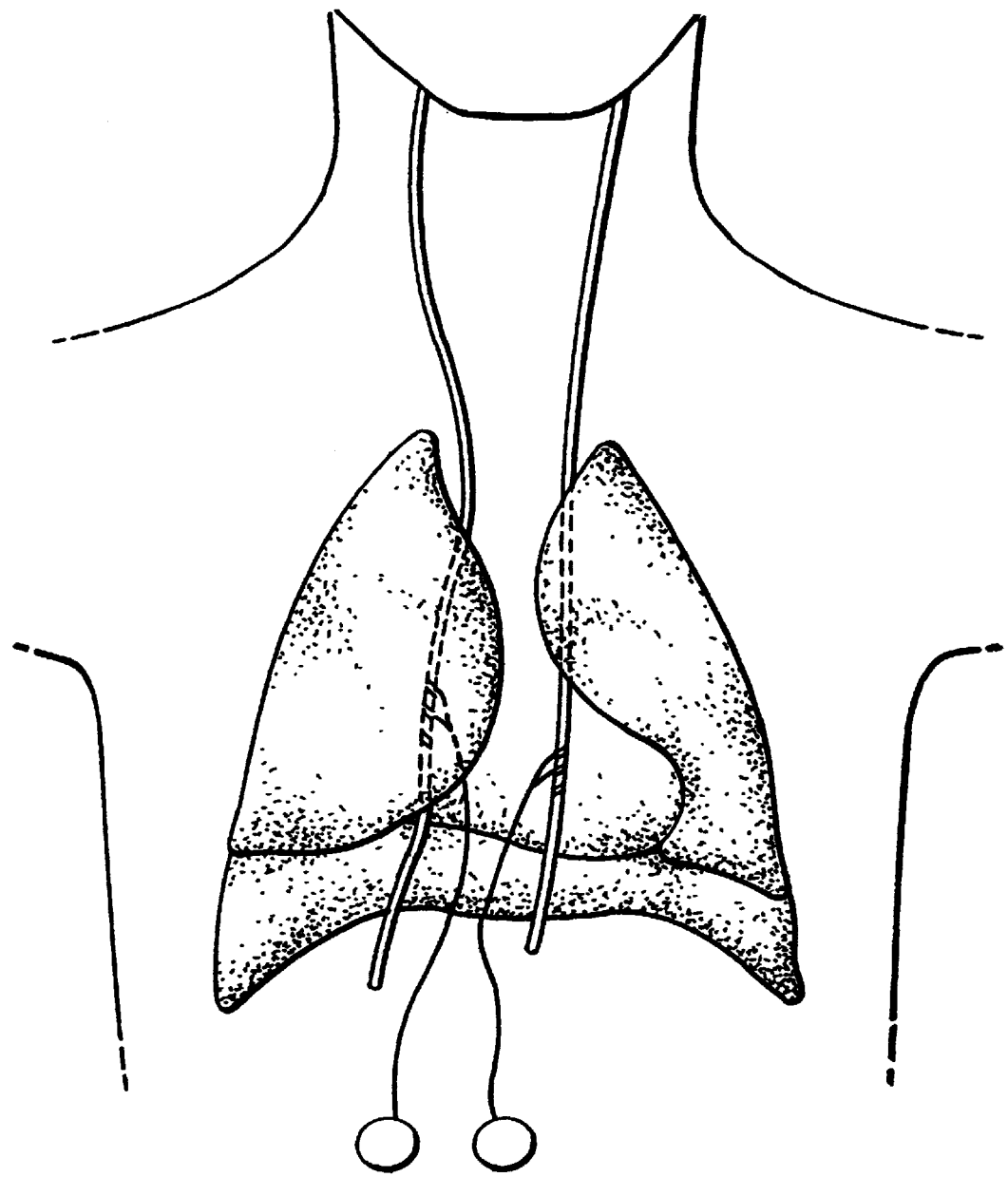

TREATMENT OF OBESITY BY BILATERAL VAGUS NERVE STIMULATION

BACKGROUND OF THE INVENTION

The present invention relates generally to methods and apparatus for treating eating disorders by application of modulating electrical signals to a selected cranial nerve, nerve branch or nerve bundle, and more particularly to techniques for treating patients with overeating disorders, and especially obese patients by application of such signals bilaterally to the patient's vagus nerve with one or more neurostimulating devices.

Increasing prevalence of obesity is one of the most serious and widespread health problems facing the world community. It is estimated that currently in American 55% of adults are obese and 20% of teenagers are either obese or significantly overweight. Additionally, 6% of the total population of the United States is morbidly obese. Morbid obesity is defined as having a body mass index of more than forty, or, as is more commonly understood, being more than one hundred pounds overweight for a person of average height. This data is alarming for numerous reasons, not the least of which is it indicates an obesity epidemic. Many health experts believe that obesity is the first or second leading cause of preventable deaths in the United States, with cigarette smoking either just lagging or leading. A recent study from the Kaiser HMO system has demonstrated that morbid obesity drastically increases health care costs (Journal of the American Medical Association (JAMA)).

It is the consequences of being overweight that are most alarming. Obesity is asserted to be the cause of approximately eighty percent of adult onset diabetes in the United States, and of ninety percent of sleep apnea cases. Obesity is also a substantial risk factor for coronary artery disease, stroke, chronic venous abnormalities, numerous orthopedic problems and esophageal reflux disease. More recently, researchers have documented a link between obesity, infertility and miscarriages, as well as post menopausal breast cancer.

Despite these statistics, treatment options for obese people are limited. Classical models combining nutritional counseling with exercise and education have not led to long term success for very many patients. Use of liquid diets and pharmaceutical agents may result in weight loss which, however, is only rarely sustained. Surgical procedures that cause either gastric restriction or malabsorption have been, collectively, the most successful long-term remedy for severe obesity. However, this type of surgery involves a major operation, can lead to emotional problems, and cannot be modified readily as patient needs demand or change. Additionally, even this attempted remedy can sometimes fail (see, e.g., Kriwanek, "Therapeutic failures after gastric bypass operations for morbid obesity," *Langenbecks Archiv. Fur Chirurgie*, 38(2): 70–74, 1995).

It is difficult to document many cases of long term success with dietary counseling, exercise therapy and behavioral modification. The introduction of pharmacologic therapy may help improve these results; however, to date pharmacologic remedies have not been able to document long term success. In addition, the chronic use of these drugs can lead to tolerance, as well as side effects from their long term administration. And, when the drug is discontinued, weight returns.

To date, surgical procedures such as gastric bypass or vertical banded gastroplasty have demonstrated the best long term success in treating people with morbid obesity. However, these operations are highly invasive and carry risks of both short and long term complications. Additionally, such operations are difficult to modify, and cannot be regulated up or down if the clinical situation changes.

As a result, a pressing need currently exists for better treatment options for obesity. The long-term failure of liquids and pharmaceuticals aptly demonstrates a need for a life-long control mechanism. A perfect treatment would be adjustable and could be regulated as needed. It would need to be with the patient at all times. The applicants herein are convinced that vagal nerve stimulation has the potential to meet those requirements as a safe and effective treatment for obesity, through an extension of the vagal stimulation technique disclosed in U.S. Pat. No. 5,263,480 to J. Wernicke et al., assigned to the same assignee as the present application. The '480 patent discloses that treatment for eating disorders in general, and obesity and compulsive overeating disorder in particular, may be carried out by selectively applying specially adapted modulating electrical signals to the patient's vagus nerve by a neurostimulator which is preferably totally implanted in the patient, but may alternatively be employed external to the body or even percutaneously. The modulating signals themselves may be stimulating or inhibiting with respect to the electrical activity of the vagus nerve, but for purposes of that patent, both cases were sometimes included within the term "stimulating". In essence, stimulation of vagal activity could cause more neural impulses to move up the nerve whereas inhibition of vagal activity could block neural impulses from moving up the nerve. The modulating signals can be used to produce excitatory or inhibitory neurotransmitter release.

According to the '480 patent, strategies for vagal modulation, including adjusting the parameters for electrical stimulation of the vagus nerve, nerve fibers or nerve bundle, depend on a number of factors. Among these are considerations of which part(s) of the nerve or the nerve fibers are to be subjected to the modulating signals; whether the patient experiences a "feeling" or sensation at the onset of the disorder or a symptom of the disorder which can be used to activate the neurostimulation generator or, alternatively, a physiologic signal is generated which can be detected and employed to trigger the modulation; and/or whether a "carryover" or refractory period occurs after modulation in which the benefit of the modulation is maintained. Further, for example, appropriate setting of pulse width and amplitude of the stimulating (modulating) signal at the output of the neurostimulator, applied via electrode(s) to the vagus nerve, might allow particular fibers of the nerve to be selectively stimulated. Also, the precise signal pattern to be used, such as the length of the time intervals in which the signal is on and off, might be adjusted to the individual patient and the particular eating disorder being treated.

In treatment of obesity, the '480 patent hypothesized that vagal stimulation could be used to produce appetite suppression by causing the patient to experience satiety, a sensation of "fullness," which would naturally result in decreased intake of food and consequent weight reduction. In effect, the brain perceives the stomach to be full as a result of the treatment.

In a then-preferred embodiment of the invention disclosed in the '480 patent for treating patients with compulsive overeating/obesity disorders, an implantable neurostimulator included a signal generator or electronics package adapted to generate an electrical output signal in the form of a sequence of pulses, with parameter values programmable by the attending physician within predetermined ranges for treating the disorder, and a lead/electrode system for applying the programmed output signal to the patient's vagus nerve. Calibration of the overall treatment system for a particular patient was to be performed by telemetry by means of an external programmer to and from the implant. The implanted electronics package might be externally programmed for activation upon occurrence of a predetermined detectable event, or, instead might be periodically or continuously activated, to generate the desired output signal with parameter values programmed to treat obesity by modulating vagal activity so as to produce a sensation of satiety.

In alternative embodiments of the invention disclosed in the '480 patent, the stimulus generator or electronics package might be located external to the patient, with only an RF coil, rectifier and the lead/nerve electrode assembly implanted; or with the lead implanted percutaneously through the skin and to the nerve electrode. The latter technique was least preferred because special precautions would be needed to avoid possible infection via the path from outside the body to the nerve along the lead.

In a preferred method of use according to the '480 patent, the stimulus generator of the neurostimulator is implanted in a convenient location in the patient's body, such as in the abdomen in relatively close proximity to the stimulating electrode system and, if applicable, to the detecting system. For treating compulsive overeating and obesity, it might be desirable to ascertain the patient's food intake, i.e., the quantity of food consumed, for example by means of implanted sensing electrodes in or at the esophagus to detect passage of food as the patient swallowed. The swallows could be summed over a preselected time interval to provide an indication or estimate of the amount of food consumed in the selected interval. Modulation of vagal activity would then be initiated if the summation exceeded a predetermined threshold level. In the preferred embodiment of the '480 patent, the stimulating electrode (nerve electrode e.g., a cuff) would be implanted about the vagus nerve or a branch thereof in the esophageal region slightly above the stomach, and the vagal stimulation applied to produce or induce satiety. As a result, the patient would experience a satisfied feeling of fullness at a level of consumption sufficient to maintain physiologic needs but supportive of weight reduction.

In another method according to the '480 patent, the appropriately programmed output signal of the neurostimulator is applied periodically to modulate the patient's vagus nerve activity, without regard to consumption of a particular quantity of food, except perhaps at prescribed mealtimes during normal waking hours according to the patient's circadian cycle. The intent of such treatment was to suppress the patient's appetite by producing the sensation of satiety between normal mealtimes.

Alternatively, or in addition to either or both of automatic detection of the event and activation of the signal generation in response thereto, or intermittent or sustained activation according to the circadian cycle, the neurostimulator electronics package could be implemented for manual activation of the output signal by the patient, as by placement of an external magnet over the implanted device (to close a switch), or by tapping the region over the device (to cause it to respond to the sound or vibration), or by use of an RF transmitter, for example. Manual activation would be useful in situations where the patient has an earnest desire to control his or her eating behavior, but requires supportive measures because of a lack of sufficient will power or self-control to refrain from the compulsive behavior, such as binge eating or simply overeating, in the absence of the neurostimulation device.

SUMMARY OF THE INVENTION

The vagus nerve is the dominant nerve of the gastrointestinal (GI) tract (see, e.g., Berthoud et al., "Morphology and distribution of vagal afferent innervation of rat gastrointestinal tract," *Soc. Neurosci. Abstr.*, 17(2), 1365, 1991). A right and a left vagus connect the GI tract to the brain. After leaving the spinal cord, the vagal afferents transport information regarding the GI tract to the brain. In the lower part of the chest, the left vagus rotates, becomes the anterior vagus, and innervates the stomach. The right vagus rotates to become the posterior vagus, which branches into the celiac division and innervates the duodenum and proximal intestinal tract. While the vagus is often thought of as a motor nerve which also carries secretory signals, 80% of the nerve is sensory consisting of afferent fibers (see, e.g., Grundy et al., "Sensory afferents from the gastrointestinal tract," *Handbook of Physiology*, Sec. 6, S.G., Ed., *American Physiology Society*, Bethesda, Md., 1989, Chapter 10).

While the exact mechanisms that make us feel full are still being determined, much information has been accumulated. Satiety signals include the stretch of mechanoreceptors, and the stimulation of certain chemosensors ("*A Protective Role for Vagal Afferents: An Hypothesis.*" *Neuroanatomy and Physiology of Abdominal Vagal Afferents*, Chapter 12. CRC Press, 1992). These signals are transported to the brain by the nervous system or endocrine factors such as gut peptides ("*External Sensory Events and the Control of the Gastrointestinal Tract: An Introduction.*" *Neuroanatomy and Physiology of Abdominal Vagal Afferents*. Chapter 5. CRC Press 1992). The role of vagal afferents in the transmission these signals has been demonstrated by numerous studies. Ritter et al. has demonstrated that direct infusion of maltose and oleic acid into the duodenum of rats leads to a reduction in oral intake. This response is ablated by vagotomy or injection of capsaicin, which destroys vagal afferents. Similarly, systemic cholecystokinin has been demonstrated to reduce intake in rats. This response is also ablated by destruction of vagal afferents. A plethora of literature makes it clear that vagal afferent fibers are an important source of information to the brain regarding the quantity and quality of the ingests.

The present invention is based on the applicants' study of particular methods and techniques of vagus nerve stimulation after numerous studies that have indicated the vagus to be an important nerve transporting satiety signals from the gut to the brain. Studies in rat models have demonstrated that the vagus nerve is the "information superhighway" for conducting signals from agents such as cholecystokinin and enterostatin. It remains to be determined whether and how such signals could be mimicked by using vagal nerve stimulation. Greater attention to use of vagal stimulation in treating obesity is also prompted in part by the knowledge that vagal nerve stimulation has been shown to be safe and effective when used long-term to treat epilepsy. That is to say, the regimen in studies involving use of vagal stimulation techniques to treat obesity would not involve the extreme measures or short- and long-term side effects on the patient that have characterized treatment methods of the type described above in the background section.

According to the present invention, a method of treating patients for obesity includes performing bilateral stimulation of the patient's vagus nerve by applying a stimulating electrical signal to the right and left vagi, wherein the parameters of the signal are predetermined to produce a sensation of satiety in the patient. The signal could be applied synchronously to the right and left vagi or asynchronously. The stimulating electrical signal is preferably a pulse signal which is applied intermittently to the right and left vagi according to the duty cycle of the signal (i.e., its on and off times). Also, the intermittent application of the stimulating electrical signal is preferably chronic, rather than acute. Nevertheless, it is possible that the bilateral stimulation could be delivered continuously to the right and left vagi to achieve some success in the treatment, and/or that acute application might suffice in some circumstances.

Also, it is conceivable that the stimulating electrical signal applied acutely to the right and left vagi during a customary mealtime, or from a short time preceding and/or following the mealtime, according to the patient's circadian cycle, could be somewhat effective in certain cases. Although an automatic delivery of bilateral intermittent stimulation is preferred, it is also possible that application of the stimulating electrical signal to the right and left vagi might be controlled by an external commencement signal administered by the patient, as by use of an external magnet brought into proximity with the implanted device.

In general, the same stimulating electrical signal is applied to both the right and left vagi, but it may also be possible to apply a different stimulating electrical signal to the right vagus from the stimulating electrical signal applied to the left vagus. Further, although two separate nerve stimulator generators may be implanted for stimulating the left and right vagi, a single nerve stimulator generator may be implanted for bilateral stimulation if the same signal is to be applied to both the left and right branches of the vagus, whether delilvered synchronously or asynchronously to the vagi.

Preferably, the stimulating electrical signal is applied at the supradiaphragmatic position of the left and right vagi. Also, the stimulating signal is characterized by a current magnitude below a predetermined physiological response to stimulation called the retching level of stimulation of the patient. This is to assure that the patient will not suffer from nausea during the periods of vagus nerve stimulation.

In summary, then, the most preferred method of treating patients for obesity, includes stimulating the left and right branches of the patient's vagus nerve simultaneously with electrical pulses in a predetermined sequence of a first period in which pulses are applied continuously, alternating with a second period in which no pulses are applied, and in which the electrical pulses are applied to the vagus nerve at a supradiaphragmatic location. The pulses preferably have an electrical current magnitude not exceeding about 6 ma, but in any event, the magnitude is preselected to be less than the level that would induce retching in the patient as determined at the time of the initial implant(s). The pulse width is adjusted to a value not exceeding about 500 ms, and the pulse repetition frequency is set at about 20–30 Hz. The second period is preferably about 1.8 times as long as the first period in the alternation of application of the stimulating pulses (i.e., the on/off duty cycle is at a ratio of 1:1.8). The pulse parameters including on time and off time are programmable by the implanting physician, using an external programmer.

Apparatus according to the invention for treating patients suffering from obesity eating disorder includes implantable neurostimulator device means for simultaneously stimulating left and right branches of the patient's vagus nerve with electrical pulses in a predetermined sequence of a first period in which pulses are applied continuously, alternating with a second period in which no pulses are applied; and electrode means for implantation on the right and left branches in a supradiaphragmatic position.

Accordingly, it is a principal objective of the present invention to provide improvements in methods and apparatus for treating and controlling overeating disorder, especially in obese patients.

It is a more specific aim of the invention to provide methods of treating and controlling compulsive overeating and obesity by bilateral intermittent pulse stimulation of the right and left vagi at a supradiaphragmatic position in the patient.

BRIEF DESCRIPTION OF THE DRAWINGS

The above and still further aims, objectives, aspects, features and attendant advantages of the present invention will be better understood from a consideration of the following detailed description of presently preferred best mode of practicing the invention, as encompassed by certain exemplary methods and embodiments thereof, taken in conjunction with the accompanying drawing, in which:

The sole FIGURE is a simplified fragmentary illustration of the stimulus generator and lead/electrode system of the neuro stimulator implanted in the patient's body.

DESCRIPTION OF THE PRESENTLY PREFERRED EMBODIMENT AND METHOD

A generally suitable form of neurostimulator for use in the apparatus and method of the present invention is disclosed in U.S. patent application Ser. No. 07/434,985, filed Nov. 13, 1989 in the names of Reese S. Terry, Jr., et al. (referred to herein as "the '985 application"), now U.S. Pat. No. 5,154,172 assigned to the same assignee as the instant application. The specification of the '985 application is incorporated herein in its entirety by reference.

According to the present invention, the patient is treated with bilateral stimulation of the right and left vagi branches at the supradiaphragmatic position of the vagus nerve, using neurostimulators (e.g., the NCP® generator available from Cyberonics, Inc. of Houston, Tex. (Cyberonics)) placed, for example, via a left anterior thoracic incision. A standard Cyberonics Bipolar Lead nerve electrode, for example, is attached to the nerve generator after the patient's eating behavior is standardized and a stable dietary pattern is observed.

In dog tests conducted by the applicants herein, the dietary pattern included twice-a-day feedings of approximately 400 grams of solid food with one scoop of soft meat product added to make the food more edible. During the surgical procedure, a threshold referred to herein as the retching threshold was documented while the animal was under anesthesia, based on the threshold value of the stimulus output current of the device at which the animal exhibited a retching or emetic response. The amount of current was adjusted to determine this threshold. Other parameters were left fixed at a frequency of 30 Hertz (Hz), a pulse width of 500 milliseconds (ms), and an on/off cycle of one minute on and 1.8 minutes off.

Following the implant of the bilateral nerve stimulators, the animals were allowed to stabilize. Once eating behavior returned to preoperative levels the vagal nerve stimulators were turned on in two canines. These two were given chronic intermittent bilateral nerve stimulation over a twenty-four hour period. Initial amplitude was set at approximately 1.0 to 1.5 milliamperes (mA) below the retching threshold, and adjusted thereafter. The retching thresholds in mA increased over a period of days.

Both chronic dogs behaved in the same manner. Initially there was no change in the eating behavior. Approximately seven to ten days later, while still being subjected to chronic intermittent bilateral nerve stimulation, eating behavior changed in both dogs. They demonstrated a lack of enthusiasm for their food, while maintaining normal behavior for all other aspects of laboratory life. Instead of consuming their meal in approximately five minutes, as had been their customary preoperative behavior, their meal consumption took between fifteen and thirty minutes. More striking was the observed manner in which they consumed the food; each of the two would eat a small portion, leave the food dish, walk around, and ultimately return to the food from what appeared to be more a case of instinct than desire.

To make certain a real effect attributable to the bilateral stimulation was being observed, after a six week period in which the intermittent stimulation was maintained, and consistent, altered eating behavior of the dogs continued, the stimulation was turned off. A of remarkable change in eating behavior was observed in each dog in one week after stimulation was discontinued, each dog exhibiting a return to its normal eating pattern after a few to several days in which it enthusiastically consumed its entire meal. Then, both stimulators were turned back on to provide the chronic intermittent bilateral stimulation in each animal, and the eating pattern of the animal slowed once again after approximately 10 to 15 days to what had been observed in the postoperative period following such stimulation.

Further study was performed to determine whether unilateral stimulation would suffice, and whether a difference could be discerned between stimulation of the right vagus versus the left vagus. With only the left nerve stimulator turned for intermittent stimulation over a period of several days, no slowing in the animal's eating behavior was observed. The left stimulator was then turned off, and the latter testing was duplicated, this time using only right vagus nerve stimulation. Once again, after a period of several days of unilateral intermittent stimulation, no slowing of the animal's eating behavior was observed.

Finally, both nerve stimulator generators were turned back on and, after a period of several days of the bilateral stimulation, each of the animal's eating behavior reverted to the slowed pace that had been observed in the postoperative period following such stimulation. The applicants postulate that these tests demonstrate that bilateral chronic intermittent stimulation is effective to change eating behavior in animals, and this same treatment is expected to be effective in changing eating behavior in obese human patients and in human patients suffering from compulsive overeating disorder, whether or not the patient is obese in the more strict sense of that term.

Moreover, the testing further demonstrated by use of acute as well as chronic stimulation that a positive response of satiety was the cause of the lack of interest of the animals in food, rather than a negative response of nausea or sick stomach. In the acute testing protocol the animals were not subjected to bilateral stimulation of the vagi until fifteen minutes to one half hour before feeding time, and throughout the meal. Such acute bilateral stimulation failed to change the eating behavior of the animals from normal baseline eating pattern to a demonstrably slowed eating pattern—change that would have been expected to occur if the stimulation had the effect of producing nausea. These tests tend to show that the slowed eating and apparent disinterest in food consumption is centrally mediated and the result of producing a sensation of satiety mimicking that which would occur after consumption of a full meal.

The characterization of the bilateral stimulation as being "intermittent" is made in the sense that the stimulation was performed following a prescribed duty cycle of application of the signal. The latter is a pulse signal, and is applied with a prescribed or preset or predetermined on-time of the pulses, followed by a prescribed or preset or predetermined off-time of the pulses, which could be the same as but in general is different from the on-time. It is possible, however, depending upon other parameters of the electrical pulse signal, that a continuous signal might be effective to produce the slowed eating behavior. It is also possible to use a single implanted nerve stimulator (pulse generator) with appropriate duty cycle to provide the bilateral stimulation of both vagal branches, right and left. Or the stimulation may be different for each branch and use different implanted stimulators. And although implanted stimulators are preferred, it is also possible to treat patients receiving clinical or in-hospital treatment by means of external devices that provide vagal stimulation via leads and electrodes implanted in the patient. Wholly implanted devices are preferred, however, because they allow patients to be completely ambulatory, and without interfering with routine daily activities.

Two other dogs with bilateral stimulators were studied in a different fashion. Initially their stimulators were left off (inactive), and were only turned on just prior to challenging the animal with food, that is, a few minutes before the meal, and during the meal. No effect on eating behavior was observed in response to such acute bilateral vagus nerve stimulation. That is, each dog followed its normal or baseline preoperative eating behavior without noticeable or perceptible slowing.

Some differences from stimulator to stimulator in magnitude of current in the pulses of the electrical stimulation signal may be observed, and may be attributable to things such as patient impedance, variation of the vagus nerve from right to left or between patients, and variation in contact between the vagus and the electrode implanted thereon from implant to implant.

Although certain preferred embodiments and methods of treating and controlling eating disorders through vagal modulation according to the invention have been described herein, it will be apparent to those skilled in the field from a consideration of the foregoing description that variations and modifications of such embodiments, methods and techniques may be made without departing from the true spirit and scope of the invention. Accordingly, it is intended that the invention shall be limited only to the extent required by the appended claims and the rules and principles of applicable law.

What is claimed is:

1. A method of treating patients for obesity, which comprises the steps of:
    performing bilateral stimulation of the patient's vagus nerve by applying a stimulating electrical signal directly and intermittently to the right and left vagi, wherein the parameters of said signal are predetermined to produce a sensation of satiety in the patient.

2. The method of claim 1, including the step of applying said stimulating electrical signal intermittently to the right and left vagi during a customary mealtime according to the patients circadian cycle.

3. The method of claim 1, including the step of applying said stimulating electrical signal intermittently to the right and left vagi upon delivery of an external commencement signal administered by the patient.

4. The method of claim 1, including the step of applying the same stimulating electrical signal intermittently to both the right and left vagi.

5. The method of claim 1, including using separate nerve stimulator generators for intermittently stimulating the left and right vagi.

6. The method of claim 1, including the step of applying said stimulating electrical signal supra diaphragmatically to the left and right vagi.

7. The method of claim 1, wherein said stimulating electrical signal is characterized by a current magnitude below a predetermined retching level.

8. The method of claim 1, wherein said stimulating electrical signal is a pulse signal having a prescribed on-off duty cycle.

9. The method of claim 8, including the step of applying said stimulating electrical signal continuously to the right and left vagi so that pulses are applied during the on portion of said duty cycle and not during the off portion of said duty cycle.

10. The method of claim 9, including using separate nerve stimulator generators for stimulating the left and right vagi.

11. The method of claim 9, including the step of applying said stimulating electrical signal supra diaphragmatically to the left and right vagi.

12. The method of claim 9, wherein one of said parameters of said stimulating electrical signal is a pulse current magnitude below a predetermined level at which the signal tends to produce retching in the patient.

13. The method of claim 9, wherein said pulse signal has a pulse current magnitude in a range up to about 6 ma.

14. The method of claim 13, wherein said pulse signal has a pulse width in a range up to about 500 ms.

15. The method of claim 14, wherein said pulse signal has a repetition frequency of about 30 Hz.

16. The method of claim 15, wherein said pulse signal has a duty cycle with a ratio of on to off of about 1:1.8.

17. The method of claim 1, wherein said electrical signal is applied synchronously to the right and left vagi.

18. A method of treating patients for obesity, which comprises the steps of:
bilaterally stimulating the patient's vagus nerve by chronically applying a stimulating electrical signal intermittently to the right and left vagi, the parameters or said signal being selected to produce a sensation of satiety in the patient.

19. A method of treating patients for obesity, which comprises the steps of:
implanting separate nerve stimulator generators into the patient, and
bilaterally stimulating The patient's vagus nerve by applying a stimulating electrical signal intermittently to the right and left vagi from said implanted separate nerve stimulator generators, the parameters of said signal being selected to produce a sensation of satiety in the patient.

20. A method of treating patients for obesity, which comprises the steps of:
implanting nerve stimulator generator apparatus into the patient, and
bilaterally stimulating the patient's vagus nerve by applying a stimulating electrical signal intermittently to the right and left vagi from said implanted nerve stimulator generator apparatus, the parameters of said signal being selected to produce a sensation of satiety in the patient.

21. A method of treating patients for obesity, which comprises the steps of:
implanting separate nerve stimulator generators into the patient, and
bilaterally stimulating the patient's vagus nerve by applying a stimulating electrical signal in the form of a pulse signal having a prescribed on-off duty cycle continuously to the right and left vagi from said implanted separate nerve stimulator generators, so that pulses are applied during the on portion of said duty cycle and not during the off portion of said duty cycle, the parameters of said signal being selected to produce a sensation of satiety in the patient.

22. A method of treating patients for compulsive overeating, which comprises the steps of:
directly stimulating the left and right branches of the patient's vagus nerve simultaneously with electrical pulses in a predetermined sequence of a first period in which pulses are applied continuously, alternating with a second period in which no pulses are applied.

23. The method of claim 22, including the step of applying said electrical pulses to the vagus nerve at a supradiaphragmatic location.

24. The method of claim 23, wherein said pulses have an electrical current magnitude not exceeding about 6 ma.

25. The method of claim 24, wherein said electrical current magnitude is preselected to be less than a level that induces retching in the patient.

26. The method of claim 25, wherein said pulses have a width not exceeding about 500 ms.

27. The method of claim 26, wherein said pulses have a repetition frequency of about 30 Hz.

28. The method of claim 27, wherein said second period is 1.8 times as long as said first period.

* * * * *